United States Patent [19]
Yamawaki et al.

[11] 4,081,994
[45] Apr. 4, 1978

[54] METHOD OF TENSION STRESS TESTING OF RUBBER

[75] Inventors: Takeshi Yamawaki, Hiratsuka; Tokitaro Hoshijima, Yokohama; Kiyoshi Mizushima, Atsugi, all of Japan

[73] Assignee: Mitsubishi Kasei Kogyo Kabushiki Kaisha, Tokyo, Japan

[21] Appl. No.: 733,867

[22] Filed: Oct. 19, 1976

[30] Foreign Application Priority Data

Oct. 20, 1975 Japan .................................. 50-126187

[51] Int. Cl.² .............................................. G01N 3/08
[52] U.S. Cl. ........................................................ 73/95
[58] Field of Search ............................ 73/95, 95.5, 78

[56] References Cited
U.S. PATENT DOCUMENTS

| 3,003,351 | 10/1961 | Ziegler et al. | 73/95 |
| 3,220,250 | 11/1965 | Strandquist et al. | 73/95 |
| 3,435,231 | 3/1969 | Griffiths et al. | 73/95 |
| 3,916,679 | 11/1975 | Voll et al. | 73/95 |

Primary Examiner—Anthony V. Ciarlante
Attorney, Agent, or Firm—Oblon, Fisher, Spivak, McClelland & Maier

[57] ABSTRACT

In a method of tension stress testing of rubber of the type wherein a rubber sample is elongated continuously at a predetermined speed and the tension stress is measured when the distance between a pair of reference positions set on the surface of the sample shows a predetermined elongation, prior to the actual test, a plurality of rubber samples having different hardness are elongated continuously under predetermined tension test conditions, the tension stress measuring time between the time of commencing the continuous elongation and a time at which the distance between the reference positions is measured, and by utilizing the data thus obtained and the data regarding the hardness of respective rubber samples, the measuring time function of the tension stress measuring time regarding the hardness is determined by a statistical method. In the actual test, the hardness of a rubber sample is measured, the tension stress measuring time is determined from the measured value of the hardness in accordance with the measuring time function, then the rubber sample is elongated continuously under said tension test conditions, and the stress is measured at the tension stress measuring time to determine the tension stress.

1 Claim, 6 Drawing Figures

METHOD OF TENSION STRESS TESTING OF RUBBER

BACKGROUND OF THE INVENTION

This invention relates to a method of tension stress testing of rubber and more particularly to an improved method of determining the tension stress of rubber by tension test.

Usually the tension stress of rubber is determined by selecting a pair of reference positions, usually established by marking a pair of reference lines on the surface of a rubber sample shaped to have a definite configuration, for example a dumb-bell shape, continuously elongating the sample at a constant or regularly varying speed and measuring the stress (the stress per unit sectional area of the rubber sample before elongation) when the distance (hereinafter termed a "reference distance" and where reference lines are used a "distance between reference lines") shows a predetermined elongation. Various methods of testing for determining the tension stress of rubber have been proposed and there are many regulations such as Japanese Industry Standard (JIS), American Standard of Testing Materials (ASTM), British Standard (BS), Deutsche Industrie-Norm (DIN) and so forth.

In the tension stress testing of rubber, usually a rubber sample marked with reference lines is mounted on a stress-electro conversion type tension tester for continuous elongation. Where a pendulum type tension tester is used an operator who watches the reference lines directly reads by himself the value of the stress which varies from time to time or causes a cooperator to read. In the former case, the reading is difficult and the accuracy is low whereas in the latter case two operators are necessary. Alternatively, a recording meter interlocked with the continuous elongation is provided in which the operator is requested to apply a signal to the recorder at a measuring point. Where a stress-electro converting type elongation tester is used, it is usual to employ a system that requests the operator to apply a signal to the recording meter.

In any one of these systems it is necessary for the operator to follow up the movement of the reference line by holding a scale for measuing the distance between the reference lines, and the accuracy of measurement greatly depends upon the response speed of the operator. For this reason, the accuracy of measurement differs greatly by the skill of the operator and measurement over a long time causes the operator to tire.

Although a number of automatic apparatus for performing tension test of rubber have also been proposed, all of them relate to automatic following up of the reference position on a rubber sample. In other words, how to eliminate the follow up scale has been the important problem.

Most of the automatic follow up devices presently available on the market can be classified into a rubber sample contacting type and a rubber sample noncontacting type. In a typical example of the former, a movable element is fixed at a reference point so as to detect the increase in the distance between reference lines, whereas in a typical example of the latter type a light beam is projected upon a reference line and the reflected light beam is detected by a photoelectric detector or a permanent magnet is mounted on a reference position and the flux of the magnet is detected by a detection coil. However, these automatic follow up devices have some disadvantages as follows. Thus, where a reference line is used, as the rubber sample elongates and deforms the width of the reference line increases proportionally so that it becomes difficult or impossible to detect it as a line. Where a detection element is secured to a reference position, the element is displaced due to the deformation of the rubber sample. In the contacting type is is necessary to mount the detection element at a correct reference position before starting of the test, and moreover since the detecting element is in contact with the sample concentrated stress may affect the elongation of the sample. In the noncontacting type the accuracy is generally low although the accuracy is determined by the characteristics of the follow up detecting element. Furthermore, as there is a limit for the response speed of the follow up driving device this type is not suitable for high speed tension test. Further, the non-contacting type automatic follow up devices generally utilize complicated mechanism and require troublesome operations.

As above described, the efforts for automation have been limited to the development of mechanical means that can be replaced for the operators action for following up the movement of the reference line by watching the same so that the type of automation as well as the accuracy thereof have been limited.

During the course of our investigation regarding the development of new automatic method of tension test of rubber we have endeavored to find out a unique relationship between various physical characteristics of rubber and the elongation thereof and found a remarkable fact that "there is a definite relationship between the hardness of rubber and a time required for the distance between reference lines reaches a predetermined value due to elongation". The invention is based on unique utilization of this fact.

SUMMARY OF THE INVENTION

Accordingly, it is an object of this invention to provide a novel method of testing tension of rubber capable of obviating various defects of the prior art method.

According to this invention there is provided a method of tension stress testing of rubber of the type wherein a rubber sample having a predetermined shape is elongated continuously at a predetermined speed and the tension stress is measured when the distance between a pair of reference positions set on the surface of the sample shows a predetermined elongation, wherein (1) prior to the actual test, a plurality of rubber samples having said predetermined shape and different hardness are elongated continuously under predetermined tension test conditions, the tension stress measuring time between the time of commencing the continuous elongation and a time at which the distance between the reference positions is measured, and by utilizing the data thus obtained and the data regarding the hardness of respective rubber samples, the measuring time function of the tension stress measuring time regarding the hardness is determined by a statistical method, and (2) in the actual test, the hardness of a rubber sample is measured, the tension stress measuring time is determined from the measured value of the hardness in accordance with the measuring time function, then the rubber sample is elongated continuously under said tension test conditions, and the stress is measured at the tension stress measuring time to determine the tension stress.

DESCRIPTION OF THE PREFERRED EMBODIMENTS

Figure 2:
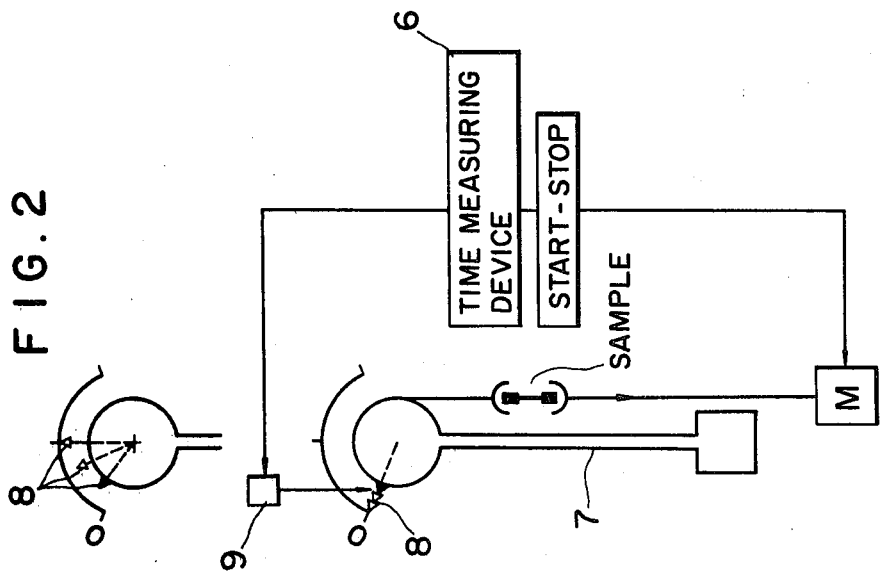
FIGS. 2 to 4 are diagrammatic representations of modified testing apparatus utilized to carry out the method of this invention.

The invention will now be described in detail.

There is no limit on the type of the rubber to be tested by the method of this invention and any type of natural and artifical rubbers can be tested, for example stylene-butadien rubbers, butadien rubbers, EPDM(ethylene-propylene terpolymers), chloroplene rubbers, nitrile rubbers, silicone rubbers, and mixtures thereof.

Also there is no limit on the shape of the rubber sample. For example, test pieces in the form of a dumbbell (form 1 - 4 defined by "The method of testing physical characteristics of vulcanized rubber" of JISK-6301, for example), a ring (form 5 and 6 defined by JISK-6301, for example), or a rectangle may be used.

As the tension tester, a pendulum type tension testing machine, and a stress-electro conversion type tension testing machine can be used.

To perform a tension test, a rubber sample is secured to driving means, such as clamps for the test piece of the tension tester. Then, the driving means are moved at a prescribed speed to continuously elongate the sample. The speed may be constant or regularly varying.

In carrying out the method of this invention, it is necessary to measure the time starting from the commencement of said continuous elongation. Usually, the starting point may be the starting point of the driving means. However, in order to eliminate any error caused by inadequate mounting of the rubber sample it is advantageous to more accurately detect the starting point of the elongation of the rubber sample itself. This can be accomplished, for example, by using a stress-electro conversion type tension tester combined with a time measuring device and a computer so as to commence the measurement of the stress concurrently with the operation of the driving means thereby detecting an instant at which stress is created due to the elongation of the rubber sample.

In carrying out the method of this invention it is necessary to determine such testing conditions as the shape of the sample, pulling speed, etc., and then determine the measuring time function under the testing conditions, the measuring time function being determined as follows.

More particularly, a number of rubber samples having different hardness levels are prepared and the hardnesses of respective samples are measured (for example, according to JISK 6301). Then, after marking reference lines, each sample is mounted on the tension tester. The sample is continuously elongated under the prescribed testing conditions while following up the movement of the reference lines with a scale, and the time between the commencement of elongation and an instant when the distance between the reference lines shows a specific elongation, that is the "tension stress measuring time" is measured. Then, by utilizing the data regarding the hardness and the tension stress measuring time thus determined, a regression curve (measuring time function) of the tension stress measuring time for the hardness is determined by a statistical method.

The concept of a regression curve is well known in statistics. Thus, where there is a pair of experimental values $(xi, yi)$ $(i = 1 - n)$ for variables $x$ and $y$ the relationship between $x$ and $y$ presumed by a statistical method (for example, by the method of least squares) is termed a regression. However, different regressions are obtained for the same pair of experimental values $(xi, yi)$ depending upon the form of the presumed type of regression curve (linear equation, quadratic equation, etc.), and upon the statiatical method relied upon. This invention is not limited to the method of obtaining the regression curve. Furthermore, in this invention, it is not essential to obtain a regression curve in the form of a mathematical equation, that is a regression equation, but it may be in the form of an equation, table or diagram so long as it can determine the relationship between the hardness and the tension stress measuring time.

The concrete form of the regression equation varies variously depending upon the tension test conditions, the method of deriving the regression equation, and the method of determining the starting point of the continuous elongation described above. However, the invention is not limited to these factors and the regression equation is determined in accordance with the accuracy, convenience or other factors.

When the measuring time function is determined, the actual test for determining the tension stress can readily be performed. More particularly, at first the hardness of a rubber sample whose tension stress is to be determined is measured and from this value the tension stress measuring time is determined according to the measuring time constant. Then, the rubber sample is mounted on a tension tester to continuously elongate the sample under said testing conditions. The time is measured starting from the commencement of the continuous elongation and the stress is measured when the tension stress measuring time is reached. At this time, a value of tension or load is generally obtained, and the stress is calculated from that value and the cross-sectional area of the sample before elongation. The value of the stress thus determined is the tension stress sought.

The detail of the actual test will now be described with referench to the accompanying drawings.

Figure 1:
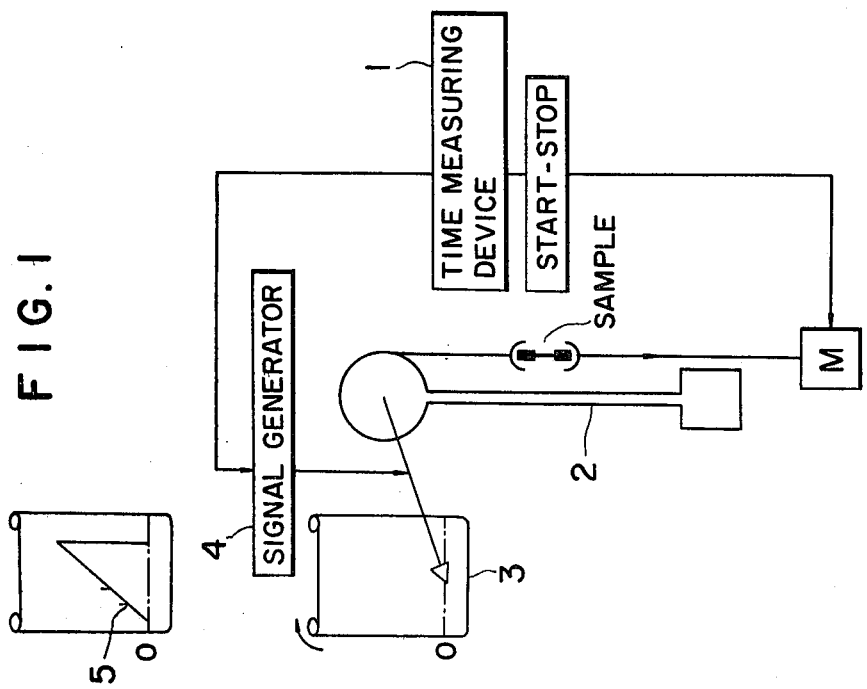
FIG. 1 is a diagrammatic representation of a testing apparatus utilized to carry out the method of this invention.

The testing apparatus diagrammatically shown in FIG. 1 is of a pendulum type tension tester comprising a time measuring device 1 which operates starting from the time of commencement of the continuous elongation, an automatic recorder 3 interlocked with a pendulum 2 and a signal generator 4. When the tension stress measuring time is reached the signal generator 4 operates to apply marks 5 on a stress-stain curve. The marks are read later to measure the tension stress as will be described later.

In the Apparatus shown in FIG. 2, a pendulum type tension tester is used and the apparatus comprises a time measuring device 6 which operates starting from the time of commencing the continuous elongation, a stress indicating pointer 8 interlocked with a pendulum and a stopping device 9 for the pointer. When the tension stress measuring time is reached, the stopping device 9 operates to stop the pointer 8 so that by reading the position of the pointer at its stopped position, the tension stress can be determined.

Figure 3:
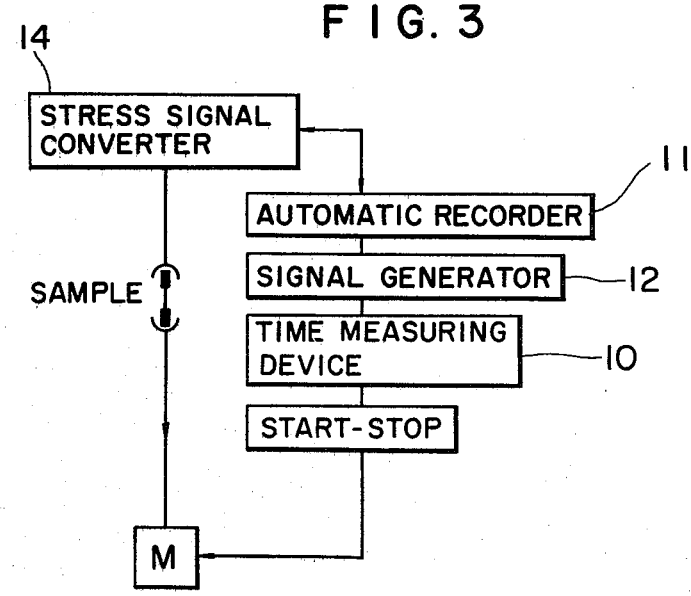

In the apparatus shown in FIG. 3 a stress-electro conversion type tension tester is used and the apparatus comprises a time measuring device 10 which operates starting from the time of commencing the continuous elongation, an automatic recorder 11 which operates in proportion to the stress, a stress signal conventer 14 and a signal generator 12 which operates to apply marks on the stress-strain curve when the tension stress measuring time is reached as has been described in connection with FIG. 1, the marks being read to determine the tension stress.

Figure 4:
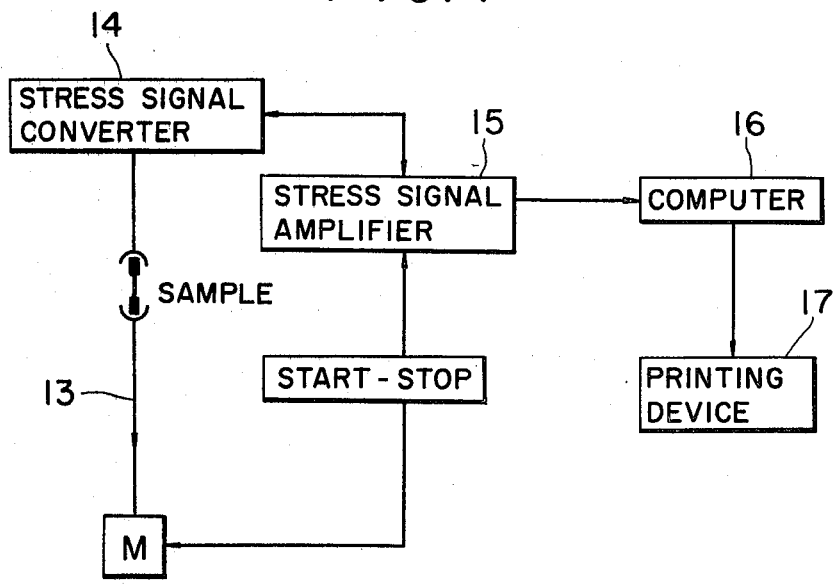

In the apparatus shown in FIG. 4, a stress-electro conversion type tester is used comprising driving means 13 for elongating a rubber sample, a stress signal convertor 14, a stress signal amplifier 15, a computer 16 (containing a time measuring device, not shown) and a printing device 17. To the input of the computer 16 are applied the hardness data regarding the hardness and the data for calculating the cross-sectional area (for example, thickness). If desired, means for detecting a time at which stress occurs in the rubber sample may be provided for the computer. The operator measures the hardness and the thickness of the sample and writes the measured values in the computer and then mounts the sample on the driving means for commencing the operation. The computer operates to calculate the tension stress measuring time and measures the tension stress at that time thereby printing the result in a predetermined form.

The invention can eliminate most of the prior art defects. First, as it is not necessary to mark the reference lines on the sample and thus labor and time can be saved. Second, since it is not necessary to follow up the movement of the reference line with a scale it is possible not only to eliminate the trouble but also operate for a long time without causing operator fatigue. Moreover it is possible to eliminate errors due to inaccurate follow up. Also it is not necessary to use complicated automatic follow up device.

In adition to various advantages described above the method of this invention can decrease the number of operators and the time required for measurement. Moreover, the required mathematical operations can readily be and automatically made, and the result of the operations can be printed in a desired from.

For a better understanding of this invention, the following example is given but it should be understood that the invention is by no means limited to the specific example.

EXAMPLE (1) Derivation of the measuring time function

A number of rubber samples having different hardness levels were prepared including natural rubbers, stylenebutadiene rubbers, butadiene rubbers, EPDM, chloroprene rubbers, nitrile rubbers, silicone rubbers and mixtures thereof.

Tension tests according to JIS K6301 were performed on these samples. The hardness of each sample was measured and then the sample was mounted on a tension tester and elongated continuously. The tension stress measuring time was measured by following up the elongation with a scale.

From the data thus obtained regarding the hardness and the tension stress measuring time the measuring time function was determined by the method of least squares. The functions obtained for respective samples are shown in the following Table. The symbols in the Table have the following meanings.

Figure 5:
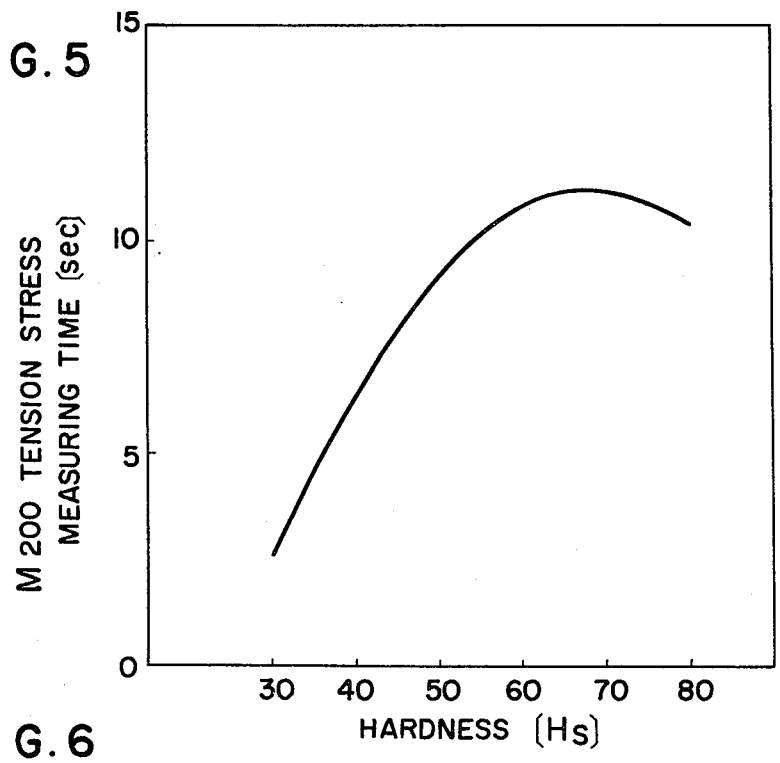
FIG. 5 is a graph showing the relationship between the hardness and the tension test measuring time for M200 (300% modulus)
Figure 6:
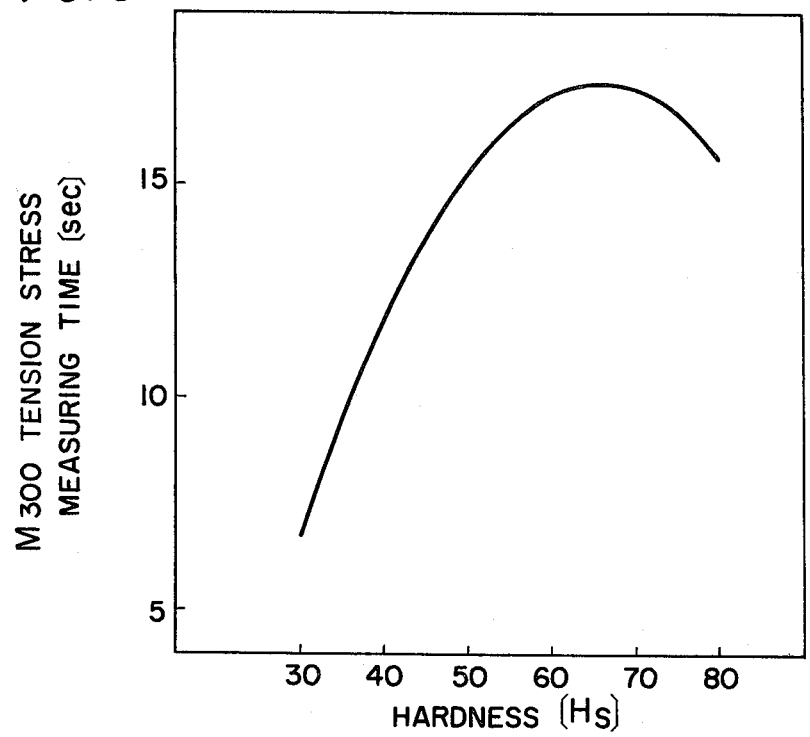
FIG. 6 is a graph similar to FIG. 5 for M300.

Mn: tension stress (kg/cm$^2$) at n% elongation
x: hardness of the sample (JIS scale Hs)
y: tension stress measuring time (Sec.)
(a) regarding M200 (200% modulus)
  linear equation: $y = 0.120x + 2.95$
  quadratic equation:
  $y = -0.00598x^2 + 0.813x - 16.4$
(b) regarding M300
  linear equation: $y = 0.123x + 9.01$
  quadratic equation: $y = -0.00863x^2 + 1.12x - 19.2$ The accuracy of the quadratic equations is higher than that of the linear equations, and FIGS. 5 and 6 show the secondary regression curves regarding M200 and M300 respectively. In each case, the reproduceability of the tension stress measuring time for the same hardness level was excellent, and it was noted that the deviations of the tension stress measuring time at various hardness from the regression curve were in a satisfactory range.

(2) Measurement of the tension stress

By using the apparatus shown in FIG. 4 the tension test was performed for a typical rubber sample to obtain the tension stress. A secondary regression curve was used as the measuring time function. A comparison between the result thus obtained and the result obtained by the prior method of following up a reference line with a scale are shown in the same Table in which the heading "automatic" shows the result of the method of this invention whereas "manual" that of the prior art method.

Table

| Sample number | M200 | | M300 | |
|---|---|---|---|---|
| | manual | automatic | manual | automatic |
| 1 | 60 | 64 | 105 | 109 |
| 2 | 61 | 62 | 105 | 106 |
| 3 | 60 | 63 | 104 | 107 |
| 4 | 61 | 64 | 107 | 108 |
| 5 | 64 | 63 | 109 | 108 |
| 6 | 60 | 63 | 105 | 108 |
| 7 | 61 | 61 | 105 | 104 |
| 8 | 62 | 64 | 104 | 108 |
| 9 | 59 | 62 | 102 | 105 |
| 10 | 61 | 62 | 106 | 106 |
| 11 | 58 | 63 | 105 | 107 |
| 12 | 61 | 62 | 109 | 106 |
| 13 | 62 | 63 | 110 | 106 |
| 14 | 62 | 63 | 105 | 106 |
| 15 | 61 | 63 | 103 | 106 |
| 16 | 61 | 62 | 105 | 106 |
| 17 | 61 | 63 | 108 | 107 |
| 18 | 62 | 62 | 106 | 107 |
| 19 | 63 | 62 | 107 | 106 |
| 20 | 62 | 63 | 105 | 107 |
| 21 | 64 | 61 | 105 | 105 |
| 22 | 58 | 63 | 102 | 106 |
| 23 | 59 | 60 | 103 | 102 |
| 24 | 61 | 63 | 105 | 107 |
| 25 | 59 | 64 | 100 | 108 |
| 26 | 60 | 59 | 105 | 103 |
| 27 | 62 | 62 | 104 | 105 |
| 28 | 60 | 62 | 104 | 105 |
| 29 | 63 | 60 | 106 | 103 |
| 30 | 60 | 63 | 107 | 106 |
| 31 | 60 | 63 | 106 | 106 |
| 32 | 60 | 62 | 104 | 105 |
| 33 | 60 | 61 | 104 | 105 |
| 34 | 60 | 62 | 104 | 105 |
| 35 | 60 | 61 | 104 | 104 |
| 36 | 61 | 63 | 109 | 106 |
| 37 | 60 | 63 | 102 | 107 |
| 38 | 61 | 63 | 101 | 107 |
| 39 | 60 | 62 | 109 | 107 |
| 40 | 59 | 62 | 107 | 106 | mean value

Table-continued

| Sample number | M200 manual | M200 automatic | M300 manual | M300 automatic |
|---|---|---|---|---|
| $\bar{x}$ | 61 | 62 | 105 | 106 |
| range (R) | 6 | 5 | 10 | 7 |
| standard deviation | 1.40 | 1.12 | 2.27 | 1.47 |

As can be noted from this table the result of this method and that of the prior art method differ only a little, yet according to the method of this invention it is possible to greatly reduce the number of operators and the measuring time.

We claim:

1. A method of tension stress testing of rubber of the type wherein a rubber sample having a predetermined shape is elongated continuously at a predetermined speed, and the tension stress is measured when the distance between a pair of reference positions set on the surface of the sample shows a predetermined elongation, wherein (1) prior to the actual test, a plurality of rubber samples having said predetermined shape and different hardness are elongated continuously under predetermined tension test conditions, the tension stress measuring time between the time of commencing said continuous elongation and a time at which said distance between said reference positions is measured, and by utilizing the data thus obtained and the data regarding the hardness of respective rubber samples, the measuring time function of the tension stress measuring time with regard to hardness is determined by a statistical method, and (2) in the actual test, the hardness of a rubber sample is measured, the tension stress measuring time is determined from the measured value of hardness in accordance with the measuring time function, then the rubber sample is elongated continuously under said tension test conditions, and the stress is measured at said tension stress measuring time to determine the tension stress.

* * * * *